(12) United States Patent
Delaage et al.

(10) Patent No.: US 7,812,952 B2
(45) Date of Patent: Oct. 12, 2010

(54) DEVICE FOR READING PLATES BEARING BIOLOGICAL REACTION SUPPORT MICRODEPOSITIONS

(75) Inventors: Michel Delaage, Marseilles (FR); Gilles Nicolaï, Sanary sur Mer (FR); Jean-Michel Decaudin, Velaux (FR); Pascal Huguet-Chantôme, Marseilles (FR)

(73) Assignee: INODIAG, La Ciotat (FR)

( * ) Notice: Subject to any disclaimer, the term of this patent is extended or adjusted under 35 U.S.C. 154(b) by 823 days.

(21) Appl. No.: 11/572,694

(22) PCT Filed: Aug. 1, 2005

(86) PCT No.: PCT/FR2005/002009

§ 371 (c)(1),
(2), (4) Date: Jan. 25, 2007

(87) PCT Pub. No.: WO2006/024772

PCT Pub. Date: Mar. 9, 2006

(65) Prior Publication Data

US 2008/0068602 A1    Mar. 20, 2008

(30) Foreign Application Priority Data

Aug. 2, 2004    (FR) .................................. 04 08520

(51) Int. Cl.
*G01J 21/25*    (2006.01)

(52) U.S. Cl. ..................................................... 356/417
(58) Field of Classification Search ................. 356/417, 356/244, 440, 326–328
See application file for complete search history.

(56) References Cited

U.S. PATENT DOCUMENTS

| 5,854,684 A | 12/1998 | Stabile et al. ................ 356/440 |
| 6,542,241 B1 | 4/2003 | Thorwirth et al. ............ 356/436 |
| 2003/0112432 A1* | 6/2003 | Yguerabide et al. ......... 356/317 |
| 2004/0032589 A1 | 2/2004 | Bechem et al. .............. 356/417 |

FOREIGN PATENT DOCUMENTS

| FR | 2 845 488 | 4/2004 |
| WO | WO 02/093144 A1 | 11/2002 |

\* cited by examiner

*Primary Examiner*—Tarifur Chowdhury
*Assistant Examiner*—Abdullahi Nur
(74) *Attorney, Agent, or Firm*—Heslin Rothenberg Farley & Mesiti P.C.

(57) ABSTRACT

A method for reading slides bearing fluorescent deposits, such as used in serology or molecular biology analysis, includes: incubating a slide with a sample of serum from a patient, or a dilution thereof, and revealing antibodies in the sample bound to the deposits by labelled reagents. Label reading and analysis is performed by a device including a slide positioner, light emitting diodes arranged in illumination channels to provide oblique illumination at different wave lengths, and a collection optic for forming an image of the deposits on a sensor.

19 Claims, 5 Drawing Sheets

Indicative dimensions : Diameter 30 mm – Length 180 mm

Sample 10344  width: 664  height: 494
nominal diameter 45

| | | | | | | | Relative fluorescences | |
| | | | | | | | zi2 | zi3 |
| number | abscissa | ordinate | area | fluo365 | fluo470 | fluo594 | IgG | IgM |
| --- | --- | --- | --- | --- | --- | --- | --- | --- |
| 1 | 230 | 236 | 1639 | 223300 | 54785 | 300 | 10000 | 82 |
| 2 | 229 | 305 | 956 | 17730 | 4808 | 350 | 11053 | 1202 |
| 3 | 229 | 373 | 1144 | 27595 | 5336 | 322 | 7881 | 710 |
| 4 | 298 | 237 | 1330 | 140214 | 2781 | 23018 | 808 | 10000 |
| 5 | 297 | 305 | 1028 | 21301 | 6200 | 374 | 11864 | 1068 |
| 6 | 296 | 373 | 1092 | 38968 | 7536 | 499 | 7882 | 781 |
| 7 | 367 | 238 | 1649 | 164389 | 86662 | 2938 | 21487 | 1089 |
| 8 | 366 | 305 | 1048 | 20001 | 4729 | 284 | 9637 | 865 |
| 9 | 366 | 374 | 1075 | 23924 | 6644 | 459 | 11319 | 1169 |
| 10 | 434 | 238 | 1133 | 76909 | 2950 | 1057 | 1564 | 837 |
| 11 | 434 | 306 | 1325 | 66973 | 7859 | 505 | 4783 | 459 |
| 12 | 433 | 375 | 1093 | 28379 | 6140 | 372 | 8819 | 798 |

Figure 5

DEVICE FOR READING PLATES BEARING BIOLOGICAL REACTION SUPPORT MICRODEPOSITIONS

CROSS REFERENCE TO RELATED APPLICATIONS

This application is a 371 national stage filing of PCT International Application No. PCT/FR2005/002009, filed on Aug. 1, 2005, and published in French on Mar. 9, 2006, as WO 2006/024772 A1, which claims priority to French application number 0408520 filed on Aug. 2, 2004, the entire disclosures of which are incorporated herein by reference.

The invention relates to a device for reading slides bearing fluorescent deposits, such as used in serology or molecular biology analysis. The invention also relates to any apparatus comprising such a device, specific implementing software, as well as the use of said apparatuses and/or devices in analytical or diagnostic methods.

BACKGROUND TO THE INVENTION

Over the past several years, multiple test devices on microscope slides, or more generally on a level support, have been developed, comprising a series of aligned deposits which are the supports of a biochemical reaction when contacted with a biological sample. After an eventual reaction with fluorescent revealing reagents, the device is read, that is to say, the reaction on each spot is quantified.

The slides may be made of glass or transparent plastic material. The number of spots on a slide can range from a few units to several thousand. The diameter of the spots is generally comprised between 50 and 250 microns. Said deposits are generally referred to as microarrays, an American term which has come into international usage.

According to a first variant, the deposits are constituted of nucleic acid sequences (DNA, deoxyribonucleic acid) and the biological sample to be tested contains a mixture of nucleic acid sequences, for example the amplified forms of its messenger RNA (ribonucleic acid) called complementary DNA (cDNA). Each deposit hybridizes with its corresponding cDNA. The hybridization reaction can be visualized and quantified by fluorescence, either by labelling the cDNA itself, or by labelling the areas of hybridization with a specific dye.

In a second variant (such as for example serological tests), the biological sample to be tested contains serum or plasma, and reacts with a slide carrying reactive elements, for example proteins, cells, subcellular fractions, bacteria, viruses, etc., placed in advance on the slide. After this first reaction, the slide is placed in contact with a revealing agent.

In all cases, it is necessary to carry out an operation whereby the signal specific to each spot is read. Said signal can be a radioisotope, a color reaction resulting from an enzymatic amplification, or else a fluorescence signal. It is in the latter case where it becomes possible to attain the resolution required by the increasing density of spots.

Whereas spotting methods have been perfected and the usefulness of multiple determinations has been confirmed, with several possible applications in the diagnostics field, there is no fluorescence reader having the required performance available at an acceptable cost to a clinical laboratory. It is in this latter category that the invention is positioned.

Currently available apparatuses make use of a laser scan to probe the slide. In general, three different lasers are necessary to acquire the different signals emitted by the spots. The image is then reconstituted on a screen and the operator visually moves a grid frame, while trying to align the mesh of the grid with the images of the spots. This operation is far from being entirely satisfactory because the spots are irregular. Of course such apparatuses are very expensive, on the order of US$ 100,000. They are designed for research purposes to process a small number of slides bearing a very large number of spots and are not adapted to the routine operations of a clinical laboratory, which processes many slides bearing a small number of spots.

There is therefore a real need for analytical microarray slide readers which enable rapid, reliable and automated analysis. In the field of serology there is in particular an unsatisfied need for a random access slide reader, which can process a slide in a short period of time (typically a few seconds) and respond to urgent diagnosis in the case of infectious diseases. The invention offers a solution to these needs.

SUMMARY OF THE INVENTION

The invention relates to a fluorescence reading device for serology or molecular biology hybridization slides. The invention also relates to any apparatus comprising one such device, and to the use of said apparatuses and/or devices in analytical or diagnostic methods. Hereinafter the terms "lighting" and "illumination" are used interchangeably to refer to fluorescence excitation light.

The object of the invention is, in particular, to provide a reading device for serology or molecular biology hybridization slides which avoids the disadvantages mentioned above, by guaranteeing that the fluorescence signals will be recorded and processed in a reliable and automatic manner. A particular feature of the devices according to this invention is based in particular on the use of light emitting diodes to supply channeled excitation light, and on the arrangement of the excitation source and the collection optic, making the reading and analysis highly reliable.

A particular object of the invention is therefore based on a device for reading and/or analyzing slides containing a reactive zone carrying microdeposits of reactive elements, said device comprising a means for positioning a slide, a means for illuminating the reactive zone and a collection optic, characterized in that:

the means for illuminating the reactive zone comprises light emitting diodes (LEDs) arranged in channels so as to enable an oblique illumination relative to the optical axis, that is to say, the axis along which the fluorescent light emitted by the microdeposits is captured by the collection optic;

the device comprises at least two channels of diodes each emitting a specific excitation light; and the collection optic contains an objective forming the image of the microdeposits on a sensor.

In an advantageous manner, the axis of the diode channels is oblique with respect to the optical axis with an angle greater than or equal to 15°; and preferably greater than or equal to 20°; and/or the device comprises at least two diodes, each diode emitting a specific illumination light having a wavelength in the near UV or in the visible region, the wavelengths being sufficiently separated so as to enable selective excitation of fluorescent molecules; preferably, the excitation wavelengths are separated by intervals greater than or equal to 100 nm; and/or the illumination light emitted by each diode follows a distinct path; and/or the device comprises elements homogenizing the illumination of the zone of deposits on the slide; and/or each channel successively contains at least one diode, a collimator, a filter intended to restrict the spectrum of excitation light emitted by said diode and, optionally, an optical device intended to homogenize the spatial distribution of the light and/or a condenser orienting the light towards the reactive zone of the slide; and/or the collection optic comprises a first objective of which one focal point coincides with the reactive zone of the slide, a filter holder, preferably a filter wheel, and a second objective forming the image; and/or the device additionally comprises a solid base and/or a console, which holds together the means of positioning the slide, the means of illuminating the reactive zone and the collection optic.

In a particular embodiment of the invention, three diodes are grouped in the same channel, in proximity to the optical axis.

In particularly preferred embodiments of the invention:

The device is commanded or operated by dedicated software, typically which corrects the signal for all causes of perturbations: randomness of spotting, irregularities of illumination and variations in the quality of the fluorescent reagents. Preferably, the software is capable of comparing the levels of fluorescence of a same spot at different wavelengths and of different spots at the same wavelength. Preferably, the software uses prerecorded images of uniform surfaces, fluorescent or simply diffusing, in order to calculate a fine correction of the fluorescence of the spots at different wavelengths; and/or the device comprises three channels of excitation light whose wavelengths are sufficiently separated to enable selective excitation of different dyes; preferably, it comprises three channels of excitation light, one centered around 365 nm, the second around 470 nm, the third around 594 nm. Other combinations of wavelengths are possible, from the near UV to the infrared; and/or the excitation light homogenization device is a light pipe with a suitable diameter to enable multiple reflections of the light, or else a device of the Kohler type. Preferably, the light homogenization device is of the Kohler type. Moreover, homogenization can be improved by adding a diffuser, for example of the holographic type; and/or when the support is a microscope slide, or any other support with parallel surfaces, the excitation light reaches the sample through the slide; and/or the objective of the collection optic on the sensor side has a focal distance less than or equal to that of the objective on the object side, generating a magnification less than or greater than 1, according to the sensor used; and/or the filter wheel is motorized and coupled to the change of excitation wavelength; and/or the collection optic forms the image of the spots on a matricial sensor, for example of the CCD type ("Charge Coupled Device"); and/or the device comprises a slide identification reader; and/or the device comprises an automatic slide feeder.

These characteristics are particularly advantageous and enable the reactive elements to be read in a reliable and automatic manner, leading to reproducible results.

A further object of the invention relates to a method of serological analysis, comprising incubating a serology slide comprising a reactive zone comprising a series of deposits of biological agents, for example infectious, pathogens, allergens or autoantigens, with a sample of serum from a patient, or a dilution thereof, then revealing antibodies (for example IgG and/or IgM) in the sample bound to the deposits by means of labelled reagents, characterized in that the reading and analysis of the label (e.g., of the fluorescence) are carried out by means of a device such as defined earlier. Preferably, the analysis method comprises three analytical wavelengths, selectively exciting three dyes: the first associated with the deposits, in advance of the serological reaction, the second associated with the revealing reagent of type G immunoglobulins and the third associated with the revealing reagent of type M immunoglobulins. In a preferred embodiment, the dye associated with the deposit can be excited at around 365 nm, the dye associated with the revealing reagent of type G immunoglobulins can be excited at around 470 nm and the dye associated with the revealing reagent of type M immunoglobulins can be excited at around 594 nm.

Another object of the invention relates to the functions of the software which runs the analysis and which preferably comprises:

the three digital images at the three wavelengths, respectively corresponding to fluorescence 1 control of the amount in the spot, fluorescence 2 measuring type G immunoglobulins and fluorescence 3 measuring type M immunoglobulins; and/or normalization of fluorescence with respect to the randomness of spotting, the non-homogeneity of illumination and the variations in the revealing reagents; and/or comparison of the signal against a positivity scale based on control sera or based on internal controls such as described in French application FR2,864,624.

The invention therefore relates to a support comprising a software system for operating a device according to the invention, implementing the formulas shown in example 3 or other similar formulas.

The invention also concerns the use of a device as defined earlier for serological or molecular biology analysis. Preferably, the molecular biology analysis comprises the analysis of ribonucleic or deoxyribonucleic acids from a biological sample. In such a case, the glass slide carries for example deposits of single stranded DNA, intended to capture fluorescent cDNAs originating from the sample. For example, the excitation wavelengths can be selected in the vicinity of 543 nm for endogenous labelling with cyanine-3, in the vicinity of 635 nm for labelling with cyanine-5, in the vicinity of 488 nm for labelling of fractions hybridized with Sybr Green® (Molecular Probes, Eugene, Oreg.). This list is not limiting.

Another aspect of the invention concerns kits, in particular for biological analysis, comprising the use of a device as defined earlier.

The invention is applicable in numerous fields, in particular for histological or serological analysis in a medical, veterinary, environmental, agri-food context, etc.

DETAILED DESCRIPTION OF THE INVENTION

As indicated above, the invention relates to a device adapted to the analysis of slides. The main constitutive elements thereof are illustrated in FIG. 1. The device advantageously comprises a solid base (1) carrying a plate (2) the purpose of which is to hold the different elements in place with respect to each other.

Each light emitting diode (3) is enclosed in a casing (4) containing the homogenization device, the whole constituting an illumination channel inserted in a support (5) on which the slide holder chamber (6) is fixed. Beyond this point is the first objective (7) which itself is inserted in a sleeve joined to the filter wheel housing (8). Symmetrically beyond the filter wheel is the second objective (9) attached to the CCD camera (10). Turning the diodes on via the control module (11), positioning the filter holder and turning on the camera are piloted by a microcomputer which also contains the analytical software according to the invention.

In a preferred embodiment, the optical axis of the collection optic is horizontal.

The light emitting diodes preferably have an electrical output comprised between 500 and 5000 mW. A set of convergent lenses is placed in front of the diodes so as to render the light beam approximately parallel. A divergence of less than 10 degrees is preferred. A specific filter to restrict the spectral window of the excitation beam is then placed. A preferred value of the window is an interval less than or equal to 40 nm.

In a preferred embodiment, the excitation wavelengths are separated from each other, one in the near UV, a second in the blue, a third in the yellow, orange or red. A preferred value for the distance between the excitation wavelengths is an interval greater than or equal to 100 nm.

In a preferred embodiment, the homogenization device is composed of a diffusing surface at the entrance of a light pipe composed of a tube of transparent material with a high index of refraction having a length preferably comprised between 20 and 40 mm, and a diameter preferably comprised between 6 and 10 mm. In such case, an input aperture concentrates the beam with a suitable angle (FIG. 2).

In another preferred embodiment, the homogenization device is composed of a diffusing surface, placed at the focal point of the collimator aperture of which one forms the image on the object (so-called Kohler assembly) (FIG. 3).

In a preferred embodiment, the diffuser is of the holographic type, with a very high yield.

In a particular embodiment, the slide to be measured is set into a moveable support which itself slides into a slot. The support is equipped with an orifice to the right of the reactive zone of the slide. A locking device, such as a thrust ball bearing, locks said support in the position where its window is in the axis of the collection optic.

In a preferred embodiment, the slide to be measured is introduced directly into the device through a slot and positioned by glide rails, and springs on the opposite side. In a preferred embodiment, the slide is equipped with a fail-safe mechanism, for example a notched corner, which prevents erroneous introduction.

The diode casing and slide housing advantageously constitute a rigid assembly which can be produced from various materials, optionally mixed. In particular it can be composed (or based on) plastic material, metal and/or any material which is rigid at temperatures of 37° C. or more. In a preferred embodiment, the block is composed of black nylon (delrin, rilsan) or anodized aluminium alloy or painted to avoid reflections.

In a preferred embodiment, the slide housing, or the moveable slide holder are made of metal in order to avoid any deformation which might be detrimental to maintaining the focus.

In a preferred embodiment, the objectives have a focal distance comprised between 20 and 40 mm. In another preferred embodiment, the camera side objective has a focal distance less than that of the object side objective. This generates a reduction which increases the capacity to capture a larger number of spots in a single image. The photoelectric matrix preferably has a number of pixels greater than 10,000.

The CCD sensor can be that of a digital camera such as Nikon's "CoolPix" or preferably a camera such as Hamamatsu 5885, Q-Imaging Qicam, Sony SVS, or any other brand. It is not necessary to cool the sensor, the oblique orientation of the excitation light guarantees an excellent signal-to-noise ratio.

In one possible embodiment, the optical axis is vertical. In a preferred embodiment, it is horizontal.

In a preferred embodiment of the inventive device, the slide protrudes from the measuring slot and enables a bar code or an electronic tag to be read. The device according to the invention therefore comprises a bar code reader or a communication antenna with the electronic tag. Thus, a particular object of the invention relates to slides equipped with electronic tags on which the characteristics and results of the reading can be recorded.

Thus, a particular object of the invention relates to the reading algorithm specific to serology slides. Three images are recorded, with three different fluorescences. The first image, which corresponds to a fluorescent tag systematically fixed to the spot at the time of slide preparation, is analyzed in terms of "clusters", that is to say of connex elements, which are the spots. The advantage of proceeding in this manner is that there is no need to position a grid on the image of the spots, which in any case would be imprecise due to unavoidable optical distortions. This also overcomes the problem of play in the slide housing glide rails and an automatic analysis becomes possible. The other two images, corresponding to two other fluorescent tags, are respectively associated with the immunoglobulin G and immunoglobulin M responses of the patient. As a major problem of the microdeposits is how much they contain, it is an element of the invention to use one of the fluorescent tags as control of the quantity of material deposited and to use the corresponding signal to correct the signals representing the serological reaction. It is another element of the invention to use the images of a slide carrying a diffusing or fluorescent element in order to measure local differences in illumination and to then use these results to correct the fluorescence of the spots for variations in illumination. It is a further element of the invention to relate the fluorescence associated with antibodies of a subject which bound to an antigen spot, to that of a reference spot of pure immunoglobulins, respectively of the G type or M type, respectively made fluorescent by the same anti-IgG and anti-IgM fluorescence revealing reagent. This will become clearer in example 3.

In a preferred embodiment, the device according to the invention additionally includes a means for moving the slide perpendicularly to the optical axis in order to be able to acquire images of different zones of the slide and thereby be able to measure a larger number of spots. According to this embodiment, up to 40,000 spots would be readable, said number being approximative, and possibly even larger depending on the spotting techniques and the number of pixels of the sensor.

In another embodiment, an automatic slide feeder is used comprising a slide rack, a slide identification reading device and a mechanical conveyor through the reading device.

The devices according to the invention are adapted to any type of microscope slide. In this context, in the context of this application, "slide" is understood as being any rigid object-carrying element which can be used for immobilizing a biological deposit, thus delimiting a reactive zone. It can be for example a solid lamella, a membrane, a filter rendered transparent, etc. The slide can be made of (or based upon) any known and conventional material such as plastic, glass, nylon, biological polymers, silica, etc. Preferred slides are glass microscope slides. Their dimensions are generally standard, i.e. approximately 26 mm×76 mm. In a preferred embodiment the slides are provided with a fail-safe mechanism, for example in the form of a notch in a corner.

In a particularly advantageous manner, in the device of the invention, the slide (or the microarrays) used for the diagnosis do not comprise more than 400 deposits, for example, which makes it possible to form the fluorescence image in a single shot. As indicated above, the slide can be positioned either by a support, or by gliding the slide into a slot. Said slot recessed in a black material, is equipped with countersinks to avoid damaging the deposits upon introduction, even erroneous.

Différents embodiments and applications of the invention are described in the examples and in the attached figures, in which:

FIG. 5 shows a print-out of the results corresponding to FIG. 4. The fluorescences of the IgG and IgM controls have been arbitrarily normalized to 10,000.

As illustrated in the figures, the invention can be used for the analysis of serology slides. In the serological mode, the slide carries a series of biological deposits ("spots"), for example of infectious, pathogenic, autoantigenic or allergenic agents. The deposits are carefully marked, said marking constituting an identification code. The liquid sample to be tested is a patient serum, generally diluted in an appropriate buffer. The treatment of the slide can be carried out by manual means, consisting of soaking in successive baths, or by automatic means such as described in patent application FR0403365.

The invention can also be implemented for molecular biology analysis, either in fluorescence mode, as described above, or in optical density mode. In the latter case, the slides carry a nylon support on which the spots are deposited, the light is diffused by the nylon and the spots absorb the light. The spots are detected and quantified as dark spots on a light background.

Other aspects and advantages of the invention will become apparent in the following examples, which must be considered as illustrative and not restrictive.

Example 1

Description of a Device According to the Invention

Figure 1:
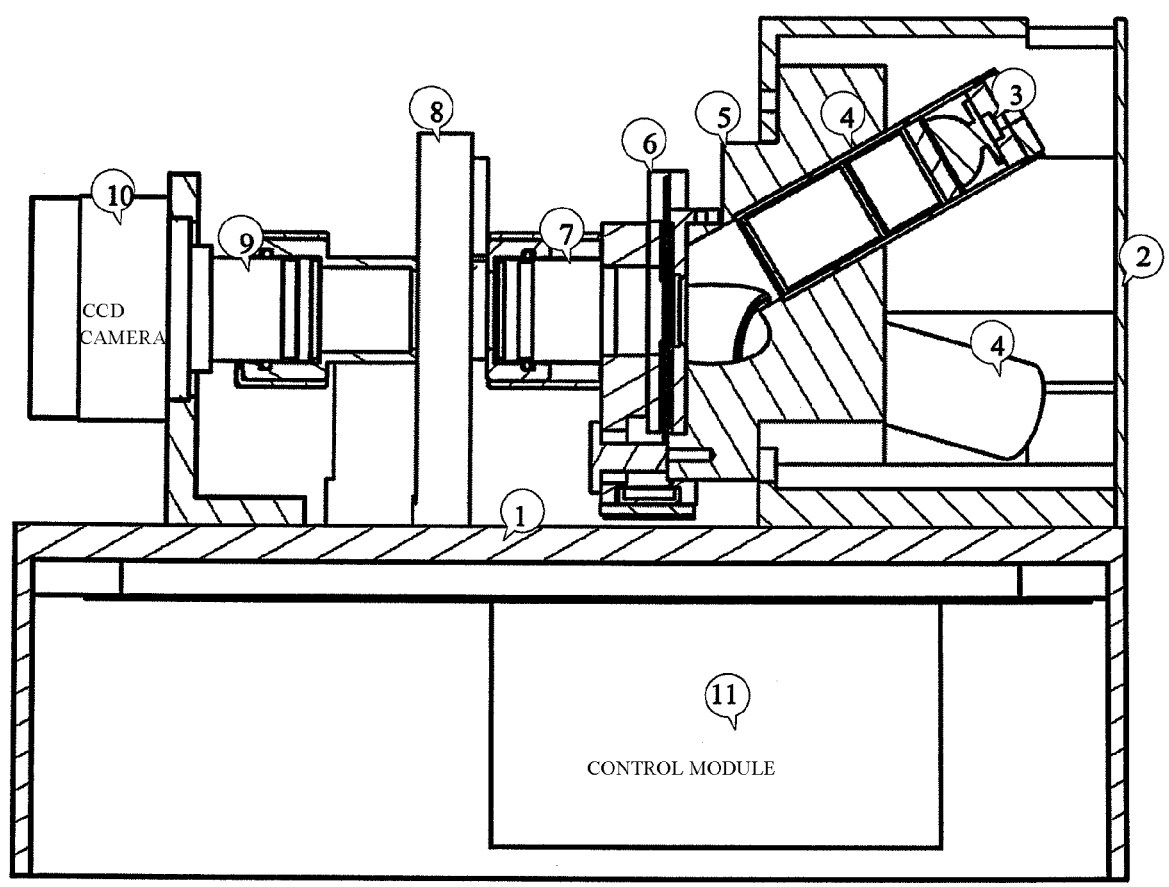
FIG. 1 is a general diagram of a device according to the invention.
Figure 2:
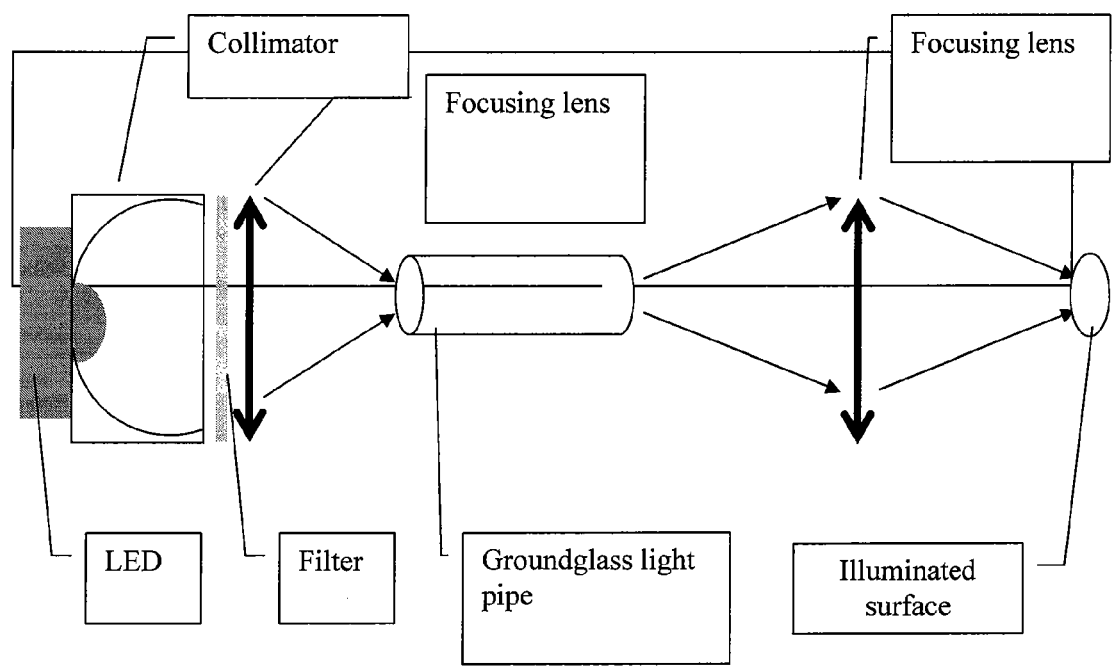
FIG. 2 is a diagram of a diode illumination channel of the light pipe type.
Figure 3:
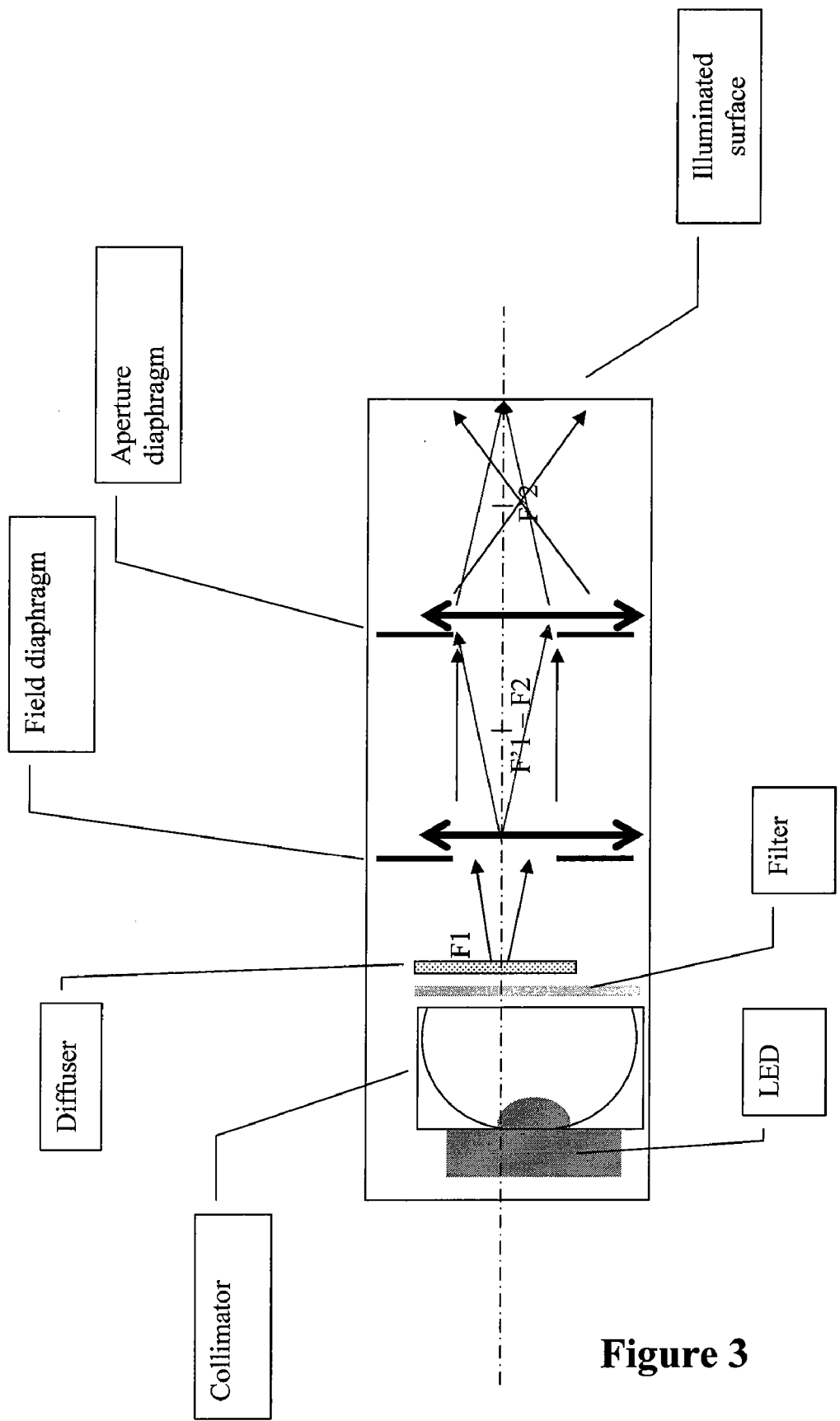
FIG. 3 is a diagram of a diode illumination channel with Kohler illumination.

This embodiment is described in relation to FIG. 1.
The light emitting diodes are:
Nichia-NCCU001 or NCCU0033 for UV excitation, associated with a Semrock FF 409-Ex02 filter;
Lumileds LXHL-MB1D for excitation at 470 nm, associated with a Semrock FF 506-Ex03 A filter;
Lumileds LXHL-ML1D for excitation at 594 nm, associated with a Chroma Technologies HQ590/40 filter.
The homogenization device is of the light pipe type.
The slide holder is made of black Delrin.
The collection optic comprises:
an infinity-corrected Fujinon f=25 mm objective;
three filters: Semrock FF 409-Em02-B, Semrock FF 506-Em02-B and Chroma HQ655/40 mounted in a linear filter holder made of black anodized aluminium;
an infinity-corrected Fujinon f=25 mm objective.
The image is projected on the sensor of a SVS Vistek SV084 "S" camera with 658×494 pixels.

The assembly is controlled by a microcomputer running implementing, reading and analytical software according to the invention.

Example 2

Description of an Analysis According to the Invention

A serology slide carries 12 spots arranged in three rows and four columns 0.5 mm apart. The first two spots on the first row are IgG and IgM immunoglobulin controls, respectively. The other spots are infectious agents.

Figure 4:
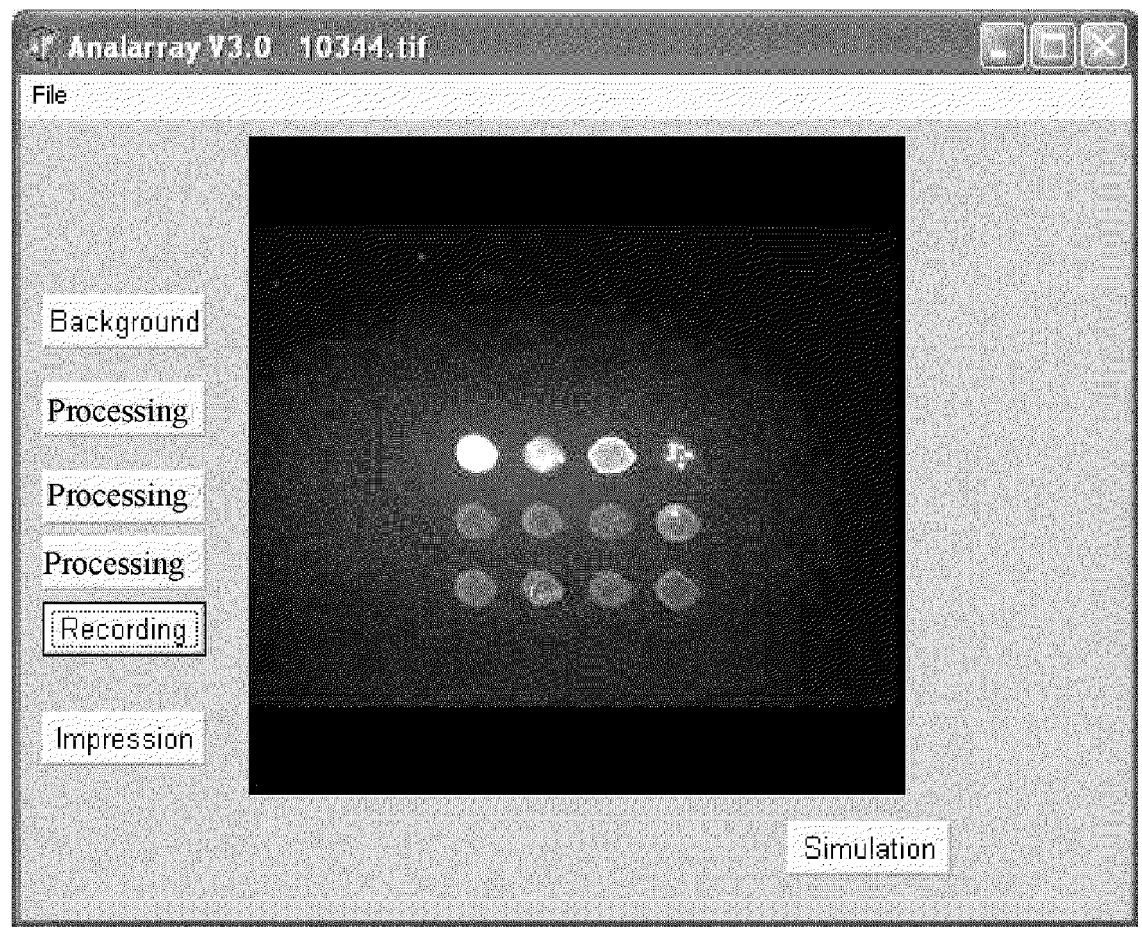
FIG. 4 represents an acquisition sequence control screen.

Before any incubation, all the spots fluoresce in the blue region under excitation at 360-380 nm. The slide is first incubated for 30 minutes with the patient's serum. Then, after rinsing, the slide is incubated for 10 minutes with a mixture of secondary antibodies: fluorescein-labelled goat anti-human immunoglobulin G antibody and Texas Red-labelled goat anti-human immunoglobulin M antibody. Spots having bound IgG show a green fluorescence excitable at 470 nm and spots having bound IgM show a red fluorescence excitable at 594 nm. Only the image excited at 365 nm is presented (FIG. 4).

Example 3

Treatment of the Signal According to the Invention

The algorithm is designed to correct the fluorescence of the spots for randomness of spotting, variations in illumination, and variations in the reagents.

Notation
$S_i$: area of spot i
The index i ranges from 1 to n, number of spots.
The value i=g corresponds to the IgG control spot, the value i=m to the IgM control spot.
$F_{ij}$: fluorescence of spot i at wavelength j, after subtracting background,
j=1: UV illumination (reference)
j=2: illumination at 470 nm
j=3: illumination at 594 nm
$E_{ij}$: illumination of area $S_i$ at wavelength j
$z_{i2}$ and $z_{i3}$ are called relative fluorescences. They are used to quantify the IgG and IgM antibody contents, specific of antigen i, in the sample.

$$z_{i2} = \frac{F_{i2}E_{i1}F_{g1}E_{g2}}{F_{i1}E_{i2}F_{g2}E_{g1}} \text{ for } IgG \text{ levels } (j=2)$$

$$z_{i3} = \frac{F_{i3}E_{i1}F_{m1}E_{m3}}{F_{i1}E_{i3}F_{m3}E_{m1}} \text{ for } IgM \text{ levels } (j=3)$$

The relative fluorescences, for example $z_{i2}$, have the expected properties. In fact:
Everything else being equal, spot size, illumination, fluorescent reagents, the relative fluorescence $z_{i2}$ is proportional to the specific signal $F_{i2}$ which represents the intensity of the serological reaction, or of the hybridization reaction.
The areas do not appear in the expression for $z_{i2}$, which therefore does not depend on the extent of spread of the deposit on the slide.

It does not depend on the amount deposited, which makes $F_{i2}$ and $F_{i1}$ for example vary in the same ratio, in the numerator and in the denominator.

It does not depend on the intensity of illumination in the zone of the deposit, which makes $F_{i2}$ and $E_{i2}$ vary in the same ratio because the fluorescence of an area is proportional to its illumination.

It does not depend on the quality of the reagent which makes $F_{i2}$ et $F_{g2}$ vary in the same ratio.

The following simplified formulas can be used, in so far as the density of the UV labelling is constant, these are the normalized fluorescences $Fn_2(i)$, $Fn_3(i)$:

$$Fn_2(i) = \frac{F_{i2}E_{g2}}{E_{i2}F_{g2}} \text{ for } IgG$$

$$Fn_3(i) = \frac{F_{i3}E_{m3}}{E_{i3}F_{m3}} \text{ for } IgM$$

which display the same properties of invariance.

The same analysis holds true for the relative fluorescence $z_{i3}$. The results corresponding to example 3 are shown in FIG. 5.

The invention claimed is:

1. A method of serological analysis, comprising (a) incubating a serology slide comprising a reactive zone comprising a series of deposits of biological agents, with a sample of serum from a patient, or a dilution thereof, then (b) revealing antibodies in the sample bound to the deposits by labelled reagents, wherein label reading and analysis are carried out by a device comprising a means for positioning the slide, a means for illuminating the reactive zone and a collection optic, wherein:
the means for illuminating the reactive zone comprises light emitting diodes arranged in illumination channels so as to enable an oblique illumination relative to an optical axis along which fluorescent light emitted by the microdeposits is captured by the collection optic;
the device comprises at least two channels of diodes each emitting a specific excitation light; and
the collection optic contains an objective forming an image of the deposits on a sensor.

2. Method according to claim 1, wherein an axis of an illumination channel of the device is oblique with respect to the optical axis with an angle greater than or equal to 15°.

3. Method according to claim 1, wherein an axis of an illumination channel of the device is oblique with respect to the optical axis with an angle greater than or equal to 20°.

4. Method according to claim 1, wherein said device comprises at least two diodes, each diode emitting a specific illumination having an excitation wavelength in the near UV or visible region, excitation wavelengths of the at least two diodes being sufficiently separated so as to enable selective excitation of fluorescent molecules.

5. Method according to claim 4, wherein the excitation wavelengths are separated by intervals greater than or equal to 100 nm.

6. Method according to claim 4, wherein the illumination emitted by each diode follows a distinct path.

7. Method according to claim 1, wherein said device further comprises elements homogenizing the illumination of the reactive zone on the slide.

8. Method according to claim 7, wherein said device comprises a Kohler type light homogenization device.

9. Method according to claim 1, wherein each channel successively contains at least one diode, a filter to restrict spectrum of excitation light emitted by said diode and an optical device to homogenize spatial distribution of the light or a condenser orienting the light towards the reactive zone of the slide.

10. Method according to claim 9, wherein the optical device intended to homogenize the spatial distribution of the light comprises a holographic diffuser.

11. Method according to claim 1, wherein the collection optic forms the image of the deposits on a CCD sensor.

12. Method according to claim 1, wherein the collection optic comprises a first objective of which one focal point coincides with the reactive zone of the slide, a filter wheel and a second objective forming the image.

13. Method according to claim 1, wherein the device further comprises an automatic slide feeding mechanism.

14. Method according to claim 1, wherein the device further comprises a solid base or a console, which holds together the means of slide positioning, the means for illuminating the reactive zone, and the collection optic.

15. Method according to claim 1, wherein said device comprises three channels of excitation light, one centered around 365 nm, a second around 470 nm, and a third around 594 nm.

16. Method according to claim 1, wherein said device is operated or commanded by software capable of carrying out comparisons of levels of fluorescence of a same spot at different wavelengths and of different spots at a same wavelength.

17. Method according to claim 16, wherein the software uses prerecorded images of uniform surfaces, fluorescent or simply diffusing, in order to calculate a fine correction of the fluorescence of the spots at different wavelengths.

18. Method of serological analysis according to claim 1, comprising three analytical wavelengths, selectively exciting three dyes: a first dye associated with the deposits, in advance of a serological reaction, a second dye associated with a revealing reagent of type G immunoglobulins and a third dye associated with a revealing reagent of type M immunoglobulins.

19. Method of serological analysis according to claim 18, wherein the first dye associated with the deposits can be excited at around 365 nm, the second dye associated with the revealing reagent of type G immunoglobulins can be excited at around 470 nm and the third dye associated with the revealing reagent of type M immunoglobulins can be excited at around 594 nm.

* * * * *